United States Patent [19]
Mehl et al.

[11] Patent Number: 5,504,239
[45] Date of Patent: Apr. 2, 1996

[54] PROCESS FOR SEPARATING OFF ALKANOLS FROM OTHER ORGANIC COMPOUNDS OF HIGHER CARBON NUMBER

[75] Inventors: Wolf Mehl, Köln; Wolfgang Scheinert, Leverkusen; Ingo Janisch, Kürten; Andreas Gröschl, Leverkusen, all of Germany

[73] Assignee: Bayer Aktiengesellschaft, Leverkusen, Germany

[21] Appl. No.: 255,025

[22] Filed: Jun. 7, 1994

[30] Foreign Application Priority Data

Jun. 14, 1993 [DE] Germany .......................... 43 19 570.9

[51] Int. Cl.⁶ .......................... C07C 27/26; C07C 29/76; C07C 69/96; C07C 41/34
[52] U.S. Cl. .......................... 558/277; 560/248; 564/216; 564/497; 568/410; 568/411; 568/699; 568/868; 568/913; 570/262
[58] Field of Search .......................... 568/913 M, 699, 568/868, 410, 411; 558/277; 560/248; 564/216, 497; 570/262

[56] References Cited

U.S. PATENT DOCUMENTS

| | | |
|---|---|---|
| 3,963,586 | 6/1976 | Ginnasi et al. . |
| 4,162,200 | 7/1979 | Himmele et al. . |
| 4,755,299 | 7/1988 | Bruschke . |
| 4,798,674 | 1/1989 | Pasternak et al. ................. 568/913 M |
| 4,876,403 | 10/1989 | Cohen et al. ....................... 568/913 M |
| 4,915,834 | 4/1990 | Bruschke . |
| 5,146,009 | 9/1992 | Cohen et al. ....................... 568/913 M |
| 5,248,427 | 9/1993 | Spiske et al. . |
| 5,294,344 | 3/1994 | Feimer et al. ........................... 568/699 |
| 5,360,923 | 11/1994 | Nickel et al. ....................... 568/913 M |

FOREIGN PATENT DOCUMENTS

| | | |
|---|---|---|
| 0001780 | 5/1979 | European Pat. Off. . |
| 0096339 | 12/1983 | European Pat. Off. . |
| 0331846 | 9/1989 | European Pat. Off. . |
| 0423949 | 4/1991 | European Pat. Off. . |
| 0476370 | 3/1992 | European Pat. Off. . |
| 2450856 | 4/1975 | Germany . |
| 2607003 | 9/1976 | Germany . |
| 2706684 | 8/1978 | Germany . |
| 2737265 | 3/1979 | Germany . |
| 3939841 | 6/1991 | Germany . |

OTHER PUBLICATIONS

Chemical Abstracts, 38–Plastics Fabr. Uses, vol. 115, 1991, p. 91; CA# 51546h, "Composite pervaporation membrane and dewatering of amines therewith", H. Brueschke et al.

Chemical Abstracts, vol. 90, 1979, p. 556; CA# 168056e, "Separation of dimethylcarbonate from its azeotrope with methanol", H. J. Buysch et al.

Chemical Abstracts, 28–Aliphatics, vol. 9, 1979, p. 601; CA# 192848f, "purification of dimethyl carbonate", K. Fischer et al.

Chemical Abstracts, 23–Aliphatics, vol. 85, 1976, p. 495; CA# 159462d, "Recovery of dimethyl carbonate from its azeotropic mixture with methanol", U. Romano.

*Primary Examiner*—Joseph E. Evans

[57] ABSTRACT

A first alkanol having from 1 to 3 carbon atoms can be separated off from other organic compounds of higher carbon number from the group comprising other alcohols, polyalcohols, ethers, oxo compounds, esters of carboxylic acids and of carbonic acid, haloaliphatics, amines, amides, hydrocarbons, carboxylic acids and nitriles, which in each case have at least 1 carbon atom more than the first alkanol, where in the case of halogenoaliphatics, halogen substituents are counted as further carbon atoms, by permeation on membranes, if a water content from 1 to 30% by weight, preferably from 5 to 15% by weight, based on the amount of mixture and water, is maintained.

19 Claims, No Drawings

PROCESS FOR SEPARATING OFF ALKANOLS FROM OTHER ORGANIC COMPOUNDS OF HIGHER CARBON NUMBER

BACKGROUND OF THE INVENTION

1. Field of the Invention

The present invention relates to a process for separating off lower alkanols from other organic compounds from the group comprising other alcohols, polyalcohols, ethers, oxo compounds, esters of carboxylic acids and of carbonic acid, halogenoaliphatics, amines, amides, hydrocarbons, carboxylic acids, nitriles or mixtures of a plurality thereof. The other organic compounds have in all cases at least one carbon atom more than the alkanol to be separated off, where in the case of halogenoaliphatics, halogen substituents are counted as further carbon atoms. The separation is carried out by pervaporation or vapour permeation on a hydrophilic membrane. For this purpose, according to the invention, a water content from 1 to 30% by weight, preferably from 5 to 15% by weight, based on the amount of mixture and water, is maintained or set and maintained.

2. Description of the Related Art

The process of the invention makes simplified separations possible, particularly in those cases where distillative separation processes fail because of the presence of an azeotrope. Even with other separation problems, the process of the invention gives substantial advantages in energy consumption. Important industrial problems of this type are, for example, the separation of methanol from i-propanol, dimethyl carbonate (DMC), methyl tert-butyl ether (MTBE) and tert-amyl methyl ether (TAME). The separation of such mixtures has hitherto been carried out, for example in the case of DMC, by two-pressure distillation (DE-A 26 07 003), since it is known that the composition of azeotropic mixtures is dependent on pressure. The degree of separation obtained by this method is often insufficient and has to be supplemented by other physical processes, for example by crystallization. In addition, pressure apparatus always result in higher capital costs; because the temperature level is increased by the pressure, increased formation of byproducts is also always to be expected. In addition to distillation under increased pressure, attempts have also been made to separate mixtures of the type described, by extractive distillation. In the case of the separation of the methanol/DMC azeotrope, water is preferably used as the extraction agent (DE-A 24 50 856). The ratio of water to dimethyl carbonate required is here 20:1. This large amount of water has to be separated from the methanol again in a further distillation column. It is an additional disadvantage here that water has more than 4 times the heat of vaporization and more than twice the thermal capacity of organic compounds; both lead to increased energy consumption. Even improvement of the extractive distillation by use of organic solvents in place of water still suffers from the disadvantage of these additives having to be worked up and recycled (EP-A 1780; DE-A 27 06 684 and DE-A 27 37 265).

There have therefore already been attempts to use membrane technology to separate mixtures which are difficult to separate. EP-A 331 846 thus describes the separation of short-chain alcohols from oxygen-containing organic compounds, such as ethers, aldehydes, ketones or esters, with the aid of a multilayer membrane. The separating membrane in this arrangement comprises either a polyvinyl alcohol membrane crosslinked with aliphatic polyaldehydes, or a resin which is also used in ion exchangers and contains acid groups which have been modified by quaternary ammonium salts. A woven polyester fabric is used as the support material for the multilayer membrane, a porous support membrane which is furthermore used comprises a woven polysulphone fabric. This membrane is a relatively complicated structure. As a result of its chemical composition, the operating temperature is limited to 70° C. and thus gives a low maximum flux of 1.5 kg/m$^2$ h. This imposes limits on industrial use. The described permeate enrichment of methanol from 73% to nearly 93% in the case of separation of methanol/DMC means that the methanol isolated by this method has to be freed from the residual 7% of DMC in a further operation.

According to the description in EP-A 423 949, an attempt is made to overcome the disadvantages described for the process of EP-A 331 846 by means of another membrane comprising a blend of polyvinyl alcohol and polyacrylic acid on polyacrylonitrile as support membrane. In the case of the separation of methanol/DMC, enrichment from 73% of methanol to about 95% of methanol is achieved at a flux of about 2 kg/m$^2$ h; this enrichment represents, on the retentate side, the minimum requirement for purified DMC for use in further processes. A membrane obtained by plasma polymerization, which is preferably a composite membrane, is, according to the description of EP-A 476 370, used for the separation of water of reaction from an esterification mixture. An esterification mixture according to this description comprises unreacted carboxylic acid, unreacted alcohol, the ester desired as the reaction product, the water of reaction formed during the reaction and an acid esterification catalyst. The separation of the water of reaction on the membrane is then followed by a separation of the retentate into the ester product stream and into the acids and alcohols which have not yet reacted and are to be recycled. The process of EP-A 476 370 is accordingly characterized in that, apart from the water, no substantial organic constituents pass through the membrane; it is particularly important here that the esterifying alcohol does not pass through the membrane.

SUMMARY OF THE INVENTION

It has now been found that $C_1$–$C_3$-alkanols can be particularly favourably separated off from their mixtures with other organic compounds containing at least one carbon atom more than this first alcohol or, for the same carbon number, additionally containing halogen atoms, if in addition to the mixture of the lower alkanol and the other compound a water content described in more detail below is maintained or set in this mixture and the separation is carried out on a hydrophilic membrane. It is possible that at the beginning of the separation of the lower alkanol the water content is the amount of water originally present in the mixture, which is supplemented, after being consumed, by the addition of further water in such a way, that the water content according to the invention is maintained until the lower alkanol has been brought to a predetermined concentration. After the separation of the $C_1$–$C_3$-alkanol, the water required for this purpose is likewise separated off. The permeate comprising the lower alkanol and water can then be worked up by known methods.

The invention accordingly provides a process for separating off a first alkanol having from 1 to 3 carbon atoms from its mixture with other organic compounds the group comprising a second straight-chain or branched, open-chain or cyclic, saturated or unsaturated $C_2$–$C_{10}$-alkanol, a $C_2$–$C_8$- polyalcohol, a straight-chain or branched, open-chain or cyclic $C_4$–$C_8$-ether or polyether, a straight-chain or branched, cyclic or open-chain $C_2$–$C_6$-oxo compound, a straight-chain, cyclic or branched $C_2$–$C_9$-carboxylic ester, a $C_3$–$C_9$-carbonic ester, a phosphoric ester having $C_1$–$C_4$-alkyl groups, a from 5 to 7-membered aromatic or nonaromatic N-heterocycle, a sulphoxide or sulphone having from 2 to 8 carbon atoms, a $C_1$–$C_4$-halogenoaliphatic, a $C_3$–$C_8$-amine, a $C_3$–$C_8$-amide, a $C_5$–$C_8$-hydrocarbon, a straight-chain or branched $C_2$–$C_6$-carboxylic acid and a $C_2$–$C_6$-nitrile, with the first alkanol always having at least one carbon atom, preferably two carbon atoms, less than each of the other organic compounds, though in the case of halogenoaliphatics, halogen substituents are counted as further carbon atoms, by pervaporation or vapour permeation, which is characterized in that the mixture described is fed, while maintaining a water content from 1 to 30% by weight, preferably from 5 to 15% by weight, based on the amount of mixture and water, at from 40° to 130° C., preferably from 40° to 100° C., to a hydrophilic membrane, with a pressure from 0.5 to 10 bar, preferably from 0.8 to 6 bar, particularly preferably from 1 to 5 bar, being set on the feed side and a pressure of at most 100 mbar, preferably at most 20 mbar, being set on the permeate side and with the permeate obtained being the first alkanol in admixture with water and the retentate obtained being the other organic compound in enriched form and with, after separating off the first alkanol, the water present being likewise separated off.

DETAILED DESCRIPTION OF THE INVENTION

For the purposes of the invention, the separation of the $C_1$–$C_3$-alkanol can be carried out from a series of compounds which are chemically different from one another and which are all miscible with such alkanols. Such compounds are:

$C_2$–$_{10}$-alkanols which can be straight-chain or branched, open-chain or cyclic, saturated or unsaturated, preferably $C_3$–$C_6$-alkanols;

$C_2$–$C_8$-polyalcohols, preferably $C_2$–$C_4$-polyalcohols;

$C_4$–$C_8$-ethers, which can be straight-chain or branched, open-chain or cyclic, preferably $C_4$–$C_6$-ethers;

$C_2$–$C_6$-oxo compounds, which can be straight-chain or branched, cyclic or open-chain, and include aldehydes and ketones;

$C_2$–$C_9$-carboxylic esters, which can be straight-chain or branched, preferably $C_3$–$C_6$-carboxylic esters;

$C_3$–$C_9$-carbonic esters, preferably $C_3$–$C_5$-carbonic esters, particularly preferably symmetrical carbonic esters;

Phosphoric esters having $C_1$–$C_4$-alkyl groups;

$C_1$–$C_4$-halogenoaliphatics;

$C_3$–$C_8$-amines;

$C_3$–$C_8$-amides;

$C_5$–$C_8$-hydrocarbons, which can be straight-chain or branched, open-chain or cyclic;

$C_2$–$C_6$-carboxylic acids, which can be straight-chain or branched, preferably $C_2$–$C_4$-carboxylic acids;

$C_2$–$C_6$-nitriles;

5- to 7-membered aromatic and nonaromatic N-heterocycles;

Sulphoxides and sulphones having from 2 to 8 carbon atoms.

Examples of such other organic compounds are: ethanol, n-propanol, i-propanol, n-butanol, i-butanol, tert-butanol, n-amyl alcohol, 3-methyl-1-butanol (i-amyl alcohol), 2-methyl-1-butanol, 2-pentanol, tert-amyl alcohol, allyl alcohol, cyclohexanol, furfuryl alcohol, hexanol, glycol, glycol monomethyl ether, glycol dimethyl ether, 1,2-propanediol, 1,3-propanediol, 1,4-butanediol, 1,6-hexanediol, glycerol, diethylene glycol, diethylene glycol monomethyl ether, tetraethylene glycol, butanetriol, diethyl ether, diisopropyl ether, dipropyl ether, methyl tert-butyl ether (MTBE), tert-amyl methyl ether (TAME), ethyl propyl ether, allyl ether, 1,4-dioxane, tetrahydrofuran, furfural, methylfurfural, acetaldehyde, propionaldehyde, acetone, butanone, methyl ethyl ketone, cyclohexanone, 2-methyl-pentanone (methyl i-butyl ketone), 2-pentanone, 3-pentanone, 1,3-dioxolane, acetonylacetone, acetylacetone, dimethyl glyoxal, diacetone alcohol, methyl acetate, ethyl acetate, n-amyl acetate, n-butyl acetate, i-butyl acetate, i-propyl acetate, i-amyl acetate, methyl formate, ethyl formate, benzyl formate, butyl formate, ethyl butyrate, i-amyl butyrate, methyl butyrate, i-butyl butyrate, butyl propionate, i-butyl propionate, i-amyl propionate, chloroacetone, trichloroethylene, tetrachloroethane, chloroform, dichloropropane, chlorobenzene, N,N-dimethylformamide, N,N-dimethylacetamide, ethanolamine, ethylenediamine, tert-amylamine, diethylamine, dichloropropane, isopropylamine, piperidine, triethanolamine, triethylamine, aniline, hexylamine, dibutylamine, benzene, toluene, xylene, kerosine, petroleum ether, cyclohexane, acetic acid, propionic acid, butyric acid, caproic acid, dimethyl carbonate, methyl ethyl carbonate, diethyl carbonate, dipropyl carbonate, dibutyl carbonate, di(i-butyl) carbonate, acetonitrile, propionitrile, butyronitrile, acrylonitrile, diethoxymethane, morpholine, N-methyl-pyrrolidone (NMP), N-methyl-caprolactam (NMC), dimethyl sulphoxide, sulpholane, picolines, pyridines, phosphoric triesters, pyridones, ethyl cyclopropylcarboxylate, cyclopropylcarboxamide, caprolactam.

It can be recognised from this list that other organic compounds which are listed in a particular group may also bear additional functional groups, such as, for example, diacetone alcohol, chloroacetone, ethanolamine, triethanolamine, etc.

It of course follows in a similar way that a low $C_1$–$C_3$-alkanol can also be separated off from a mixture of a plurality of the other organic compounds listed above. Such mixtures are, for example, ethyl acetate/ethanol, diethyl ether/ethanol, acetates/ethanol, acetone/i-propyl ether, allyl alcohol/allyl ether, allyl alcohol/cyclohexane, benzene/ethanol, butanol/butyl acetate, butanol/dibutyl ether, chloroform/ethanol, ethanol/ethyl butyl ether, propyl acetate/propanol, isopropyl ether/i-propanol, ethanol/i-propanol, ethyl acetate/ethanol/acetic acid and further combinations which can easily be derived from the above list.

The other organic compound from which a $C_1$–$C_3$-alkanol is separated off according to the invention is preferably one from the group comprising the abovementioned $C_2$–$C_{10}$-alcohols, the $C_2$–$C_8$-polyalcohols, the $C_4$–$C_8$-ethers, the $C_2$–$C_6$-oxo compounds, the $C_2$–$C_9$-carboxylic esters, the $C_3$–$C_9$-carbonic esters, the $C_3$–$C_8$-amines, the $C_3$–$C_8$-acid amides and the $C_2$–$C_6$-carboxylic acids. Particular preference is given to the other organic compound coming from the group comprising the $C_2$–$C_{10}$-alcohols, the $C_4$–$C_8$-ethers, the $C_2$–$C_6$-oxo compounds, the $C_2$–$C_9$-carboxylic esters or the $C_3$–$C_9$-carbonic esters.

$C_1$–$C_3$-alkanols which are separated off from other organic compounds are methanol, ethanol, n-propanol or i-propanol, preferably methanol or ethanol, particularly preferably methanol. A mixture of a plurality thereof can also be separated off.

Particularly important separation tasks in industrial chemistry are: the separation of methanol from a mixture thereof with another organic compound from the group comprising straight-chain or branched $C_3$–$C_6$-alkanols, DMC, MTBE or TAME.

The process of the invention is carried out at a feed temperature from 40° to 130° C., preferably from 40° to 100° C. On the feed side, a pressure from 0.5 to 10 bar, preferably from 0.8 to 6 bar, particularly preferably from 1 to 5 bar, is set. On the permeate side, a pressure of at most 100 mbar, preferably at most 20 mbar, for example from 1 to 100 mbar, preferably from 1 to 20 mbar, is set.

In carrying out the process of the invention as pervaporation, the feed mixture is brought up to the membrane in liquid form and the pressure and the temperature on the feed side are set in such a way that the pressure lies at the boiling pressure or above the boiling pressure of the feed mixture. In a preferred embodiment, the pervaporation is carried out in such a way that the feed mixture is supplied to the membrane in boiling form.

However, it is likewise possible to carry out the process of the invention in the form of vapour permeation, with the feed mixture being brought to the membrane in vapour form. In this case, the pressures and temperatures are selected and combined within the specified ranges in such a way that the pressure, as a function of the temperature, lies below the vapour pressure of the feed mixture. If desired, in the case of vapour permeation, the feed mixture in vapour form can be brought up to the membrane with the aid of a carrier gas stream comprising an inert gas or a mixture of a plurality of inert gases. Inert gases which can be used are, for example, nitrogen, the noble gases, lower hydrocarbons, air, carbon monoxide or carbon dioxide.

The permeate is initially obtained in vapour form and can be conducted away from the membrane in this form or can be first condensed and taken from the permeate space as condensate. In the case of gaseous removal, an inert carrier gas of the above described type can also be used here.

The construction of an apparatus for carrying out the process of the invention is simple and comprises a reservoir for the mixture to be separated, a pump for setting the desired feed pressure, a module with the hydrophilic membrane to be used according to the invention, a means of removing the retentate remaining on the inflow side of the membrane and a means of removing the permeate, with the latter function being characterized above all else by the vacuum pump required for maintaining the reduced pressure. The permeate side can have a condenser upstream or downstream of the vacuum pump. It is furthermore possible for the process of the invention to be operated pseudobatchwise by treatment of a predetermined amount of mixture, or to be operated in a fully continuous manner. In batchwise operation, it is furthermore possible for the retentate to be recycled to the reservoir of mixture to be separated, and thus for the batch of mixture to be brought repeatedly to the membrane until the desired degree of separation is achieved. In the case of fully continuous operation, it is furthermore possible to bring the retentate to a further module and thus to carry out a multistage treatment until the desired degree of separation is achieved.

According to the invention, the amount of water added to the feed mixture is that required to maintain a water content from 1 to 30% by weight, based on the amount of mixture and water. Preferably, a water content from 5 to 15% by weight is maintained. This water is either mixed into the mixture of lower alkanol and other organic compound to be separated prior to this mixture entering the membrane module, or simultaneously supplied to the inflow side of the membrane via a separate line. It is furthermore possible, and corresponds to the realities of industrial chemistry, for the mixtures to be separated to already contain water. However, this water content originally introduced into the reaction with the mixture to be separated is supplemented, after being consumed, by water added according to the invention in the further course of the process, in such a way that the abovementioned amount of water is continually maintained in the mixture to be separated in the membrane module. After separating off the $C_1$–$C_3$-alkanol from the other organic compound, optionally up to a predetermined extent, residual water still present is separated off in such a way that the other organic compound is obtained free of $C_1$–$C_3$-alkanol and free of water, or contains amounts of these materials below a predetermined upper specification limit.

The process of the invention is carried out on a hydrophilic membrane. Such membranes can be produced, for example, from cellulose diacetate, cellulose triacetate or polyvinyl alcohol or be a pore-free layer produced by plasma polymerization. The polymer materials here frequently have a molecular weight between 15,000 and 200,000. Polyvinyl alcohol is generally prepared by substantial saponification of polyvinyl acetate; the degrees of saponification should preferably be above 95%, particularly preferably above 98%. Owing to the water-solubility of polyvinyl alcohol, this is generally used in crosslinked form. Such crosslinking can be by etherification, esterification or acetal formation with polyfunctional compounds. Such membranes are, in principle, known to those skilled in the art.

Preference is given to using composite membranes which generally comprise a plurality of layers, viz. a base layer, a porous support layer and the actual separating layer (EP-A 96 339; DE-A 39 39 841). Suitable base layers are, in general, highly porous flexible woven fabrics or nonwovens made of fibres including metal fibres, polyolefins, polysulphones, polyetherimides, polyphenylene sulphides or carbon; porous structures made of glass, ceramic, graphite or metals are likewise suitable. The porous support layer preferably has an asymmetric pore structure. Such porous support layers can be produced, for example, from polysulphone, polyether sulphone, polyetherimide, polyvinylidene fluoride, hydrolysed cellulose triacetate, polyphenylene sulphide, polyacrylonitrile, polytetrafluoroethylene, polyethylene, polyvinyl alcohol, copolymers of trifluorinated polyolefins, and from other suitable polymers. The molecular weights can likewise lie in the range from 15,000 to 200,000. The actual separating layer can in turn comprise cellulose diacetate, cellulose triacetate or polyvinyl alcohol. Polyvinyl alcohol is crosslinked in the above described manner to better resist attack by water at elevated temperatures.

The process of the invention for separating off $C_1$–$C_3$-alkanols from other organic compounds of higher carbon number in the presence of water gives significant advantages in comparison with the hitherto known separation of this type without the accompanying use of water. Thus, an increased flux of the alkanol to be separated off is observed, although it would have been expected that the hydrophilic membrane would predominantly allow only the water to pass through, with the alkanol remaining in the retentate with the other organic compounds. However, in actual fact the opposite is the case, viz. the water passing through acts as a type of entrainer for the lower alkanol so that the increased flux allows the specific membrane area required to be greatly reduced. If, for example, the membrane area required in the pervaporation of methanol from i-propanol as the other organic compound is taken as 100%, then this membrane area requirement can be reduced to 16% of the previous value by maintaining from about 8 to 10% by weight of water in a methanol/i-propanol mixture during pervaporation.

EXAMPLES

Example 1

In the vapour permeation of methanol from i-propanol as the other organic compound, the membrane area requirement can be reduced to 10% by adding water to the methanol/i-propanol mixture until the water content is from about 8 to 10% by weight and maintaining the said water content during vapour permeation.

Example 2

In the vapour permeation of methanol from dimethyl carbonate as the other organic compound, the permeation of methanol is only made possible by adding water to a methanol/dimethyl carbonate mixture until the water content is from about 8 to 10% by weight and maintaining the said water content during vapour permeation.

What is claimed is:

1. A process for separating off a first alkanol having from 1 to 3 atoms from its mixture with other organic compounds selected from the group consisting of a second straight-chain or branched, open-chain or cyclic, saturated or unsaturated $C_2$–$C_{10}$-alkanol, a $C_2$–$C_8$-polyalcohol, a straight-chain or branched, open-chain or cyclic $C_4$–$C_8$-ether or polyether, a straight-chain or branched, open-chain or cyclic $C_2$–$C_6$-oxo compound, a straight-chain, cyclic or branched $C_2$–$C_9$-carboxylic ester, a $C_3$–$C_9$-carbonic ester, a phosphoric ester having $C_1$–$C_4$-alkyl groups, a from 5- to 7-membered aromatic or nonaromatic N-heterocycle, a sulphoxide or sulphone having from 2 to 8 carbon atoms, a $C_1$–$C_4$-halogenoaliphatic, a $C_3$–$C_8$-amine, a $C_3$–$C_8$-acid amide, a $C_5$–$C_8$-hydrocarbon, a straight-chain or branched $C_2$–$C_6$-carboxylic acid and a $C_2$–$C_6$-nitrile, with the first alkanol always having at least one carbon atom less than each of the other organic compounds, though in the case of halogenoaliphatics, halogen substituents are counted as further carbon atoms, by pervaporation or vapour permeation, wherein the mixture described is fed, while maintaining a water content from 1 to 30% by weight, based on the amount of mixture and water, and wherein water is added in the course of the process in the amount necessary to maintain said water content, at from 40° to 130° C. to a hydrophilic membrane, said membrane being a composite membrane comprising a support material and a layer of cellulose diacetate, cellulose triacetate or polyvinyl alcohol applied thereon or a pore-free layer applied by plasma polymerization, with a pressure from 0.5 to 10 bar being set on the feed side and a pressure of at most 100 mbar being set on the permeate side and with the permeate obtained being the first alkanol in admixture with water and the retentate obtained being the other organic compound in enriched form and with, after separating off the first alkanol, the water present being likewise separated off.

2. The process of claim 1, wherein the first alkanol has at least two carbon atoms less than each of the other organic compounds.

3. The process of claim 1, wherein a water content from 5 to 15% by weight, based on the amount of mixture and water, is maintained.

4. The process of claim 1, wherein the mixture is fed at from 40° to 100° C. to the membrane.

5. The process of claim 1, wherein the mixture is fed to the membrane with a pressure from 0.8 to 6 bar on the feed side.

6. The process of claim 5, wherein the mixture is fed to the membrane with a pressure from 1 to 5 bar on the feed side.

7. The process of claim 1, wherein a pressure of at most 20 mbar is set on the permeate side.

8. The process of claim 1, wherein the first alkanol is ethanol or methanol or a mixture of the two.

9. The process of claim 8, wherein the first alkanol is methanol.

10. The process of claim 1, wherein the first alkanol is separated off from other organic compounds from the group comprising $C_2$–$C_{10}$-alcohols, $C_2$–$C_8$-polyalcohols, $C_4$–$C_8$-ethers, $C_2$–$C_6$-oxo compounds, $C_2$–$C_9$-carboxylic esters, $C_3$–$C_9$-carbonic esters, $C_3$–$C_8$-amines, $C_3$–$C_8$-acid amides and $C_2$–$C_6$-carboxylic acids.

11. The process of claim 10, wherein the first alkanol is separated off from other organic compounds from the group comprising $C_2$–$C_{10}$-alcohols, $C_4$–$C_8$-ethers, $C_2$–$C_6$-oxo compounds, $C_2$–$C_9$-carboxylic esters and $C_3$–$C_9$-carbonic esters.

12. The process of claim 8 wherein methanol is separated off from a mixture thereof with one other compound from the group comprising straight-chain or branched $C_3$–$C_6$-alkanols, dimethyl carbonate, methyl tert-butyl ether or tert-amyl methyl ether.

13. The process of claim 1, wherein, when carried out as pervoration the feed pressure, as a function of the temperature, is set in such a way that it lies at the boiling pressure or above the boiling pressure of the feed and when carried out as vapour permeation the feed pressure, as a function of the temperature, is set in such a way that it lies below the vapour pressure of the feed.

14. The process of claim 1, wherein the water content at the beginning of the reaction is that amount of water originally present in the mixture and in the further course of the process water is added in the amount required to maintain a water content from 1 to 30% by weight, based on the amount of mixture and water.

15. The process of claim 14, wherein in the further course of the process water is added in the amount required to maintain a water content from 5 to 15% by weight, based on the amount of mixture and water.

16. The process of claim 1, wherein the support material is a porous polymer.

17. The process of claim 16, wherein the support material is a porous asymmetric polymer.

18. The process of claim 1, wherein the support material is based on polyacrylonitrile, polysulphone, polytetrafluoroethylene, polyethylene, polyvinyl alcohol, polyethersulphone, polyetherimide, polyvinylidene fluoride, hydrolysed cellulose triacetate, polyphenylene sulphide or copolymers of partially fluorinated polyolefins.

19. The process of claim 1, wherein the layer applied comprises polyvinyl alcohol or crosslinked polyvinyl alcohol.

* * * * *

UNITED STATES PATENT AND TRADEMARK OFFICE
CERTIFICATE OF CORRECTION

PATENT NO. : 5,504,239
DATED : April 2, 1996
INVENTOR(S) : Mehl, et al.

It is certified that error appears in the above-indentified patent and that said Letters Patent is hereby corrected as shown below:

| | |
|---|---|
| Title Page | After and under " Primary Examiner- Joseph E. Evans " Insert -- Attorney, Agent, or Firm- Sprung Kramer Schaefer & Briscoe -- |
| Title Page | Last line delete " 19 Claims " and substitute -- 18 Claims -- |
| Col. 8, claim 14 lines 1-6 | Delete " 14. The process of claim 1, wherein the water content at the begining of the reaction is that amount of water originally present in the mixture and in the further course of the process water is added in the amount required to maintain a water content from 1 to 30% by weight, based on the amount of mixture and water. " |
| Col. 8, line 48 | Delete claim " 14 " and substitute --1 -- |

Signed and Sealed this

Third Day of February, 1998

Attest:

BRUCE LEHMAN

Attesting Officer

Commissioner of Patents and Trademarks